US011331226B2

(12) United States Patent
Mihali et al.

(10) Patent No.: US 11,331,226 B2
(45) Date of Patent: May 17, 2022

(54) BIOFLUIDS DETECTION AND NOTIFICATION SYSTEM AND METHOD

(71) Applicant: Vener8 Technologies, Southport, CT (US)

(72) Inventors: Raul C. Mihali, Westport, CT (US); Dorin E. Calbaza, Cohoes, NY (US); Jonathan A. Glass, Riverside, CT (US); Anton R Simunovic, Westport, CT (US); Avdhoot Saple, Watervliet, NY (US)

(73) Assignee: VENER8 TECHNOLOGIES, Southport, CT (US)

( * ) Notice: Subject to any disclaimer, the term of this patent is extended or adjusted under 35 U.S.C. 154(b) by 459 days.

(21) Appl. No.: 15/814,635

(22) Filed: Nov. 16, 2017

(65) Prior Publication Data

US 2020/0297548 A1 Sep. 24, 2020

Related U.S. Application Data

(60) Provisional application No. 62/423,811, filed on Nov. 18, 2016.

(51) Int. Cl.

*A61F 13/42* (2006.01)
*G01N 27/04* (2006.01)

(52) U.S. Cl.

CPC .......... *A61F 13/42* (2013.01); *G01N 27/048* (2013.01); *A61F 2013/424* (2013.01)

(58) Field of Classification Search

CPC ...... A61F 13/42; A61F 2013/424; A61F 5/48; G01N 27/048; G01N 27/04; G08B 21/20; G01M 3/16

See application file for complete search history.

(56) References Cited

U.S. PATENT DOCUMENTS

2006/0192679 A1* 8/2006 Buckley .............. G01F 23/2885 340/618
2014/0190830 A1* 7/2014 Sturmer ............ B01L 3/502792 204/452
2015/0157512 A1* 6/2015 Abir ......................... A61B 5/08 340/573.5

* cited by examiner

*Primary Examiner* — Jermele M Hollington
*Assistant Examiner* — Suresh K Rajaputra
(74) *Attorney, Agent, or Firm* — Meagher Emanuel Laks Goldberg & Liao, LLP

(57) ABSTRACT

A system and method for detecting biofluid is disclosed, specifically utilizing a signaling element and a reader, wherein the signaling element comprises a sensing element, an impedance measuring circuit, an oscillator circuit, an acoustic transducer, and a power supply source, while the reader device comprises a microphone and a processor.

14 Claims, 15 Drawing Sheets

BIOFLUIDS DETECTION AND NOTIFICATION SYSTEM AND METHOD

TECHNICAL FIELD

This invention relates to a system and method for detecting and signaling the presence of moisture, such as biofluids, especially in hospitals, long-term care facilities, post-acute care facilities, or home healthcare settings.

BACKGROUND ART

Pressure ulcers, also known as pressure sores, decubitus ulcers, pressure injuries and bedsores, are a significant patient care issue in acute and post-acute care settings. Pressure ulcers are injuries to the skin and surrounding tissues resulting from prolonged pressure in one area of the skin and typically result from a patient sitting or lying in one position for too long while bedridden or wheel chair confined. In the U.S. alone, these injuries affect 2.5 to 3 million adults and result in approximately 60,000 deaths annually from related complications and infections. Accordingly, pressure ulcers place a significant financial burden on U.S. healthcare resources. In the U.S., the Centers for Medicare & Medicaid Services has estimated that each pressure ulcer case adds $43,180 in hospital costs and that pressure ulcers overall add up to $11 billion in annual costs to the U.S. healthcare system. Moreover, pressure ulcers are the second most common claim after wrongful death against U.S. healthcare providers and account for 17,000 lawsuits annually.

Prolonged patient exposure to moisture—such as moisture from urinary or diarrheal incontinence—can accelerate the development of a pressure ulcer or other forms of skin injury, such as cellulitis or dermatitis, or exacerbate an existing injury. Thus, real-time detection of a moisture event and notification to nursing personnel may have a significant positive impact in reducing skin injury incurrence and/or severity and electrode to improved quality of care and reduced financial and legal burdens for acute, post-acute, long-term and home health care providers.

However, no commercially-available clinical moisture detection and notification system presently exists that is (i) easy to use, and performance- and cost-effective for the care provider, and (ii) comfortable and unobtrusive for the patient. Further, commercially-available solutions typically require that a portion of the system be cleaned or sterilized after each moisture event, as they are too expensive to be discarded, thus increasing costs and requiring additional time from the care provider staff to replace the cleaned or sterilized portion and ensure the system is functioning properly. Further still, such systems are not compatible with and must be used instead of the sanitary articles that caregivers typically use to collect and/or absorb biofluids, such as disposable incontinence pads and briefs.

Current wetness detection systems also have problems with cost effective ways of detecting moisture when more than one individual is in a room. Current techniques utilize either obtrusive audio alarms built into the device, or more expensive RF devices. Thus, there exists a need for an inexpensive, unobtrusive, long-lasting, non-RF device that can monitor patient wetness accurately in situations where more than one patient are in a room.

SUMMARY

Sensing elements, systems, and methods for detecting biofluids are described. In one aspect, a sensing element comprises a plurality of conductive, interdigitated patterns on a substrate. The sensing element may advantageously include a bridging pattern between fingers. The sensing element may advantageously also comprise at least one molecule configured to react with a specific analyte or analytes within a biofluid.

In one aspect, a system can be used to detect biofluids, where the system comprises a signaling device including a sensing element and other circuitry, as well as a reader device including a microphone and a processor adapted for completing a Fast Fourier Transform (FFT) and filtering the results for a predetermined frequency range, typically between 16 and 20 kHz. The system may advantageously also comprise various additional features, such as a visual indicator or a timer.

In one aspect, a system can be used to detect wetness events, by first measuring impedance, determining if it is greater than or equal to a threshold value, and sending an acoustic signal, then processing the signal to determine if a wetness event has occurred, and sending notifications and handling data as needed. The system may advantageously also further repeat certain steps if a predetermined threshold of the maximum amplitude of the filtered results does not occur a predetermined number of times.

DETAILED DESCRIPTION

The present invention is directed to methods and apparatus for detecting moisture using a reader which can detect audio signals of greater than 12 kHz and determine of an event has been signaled by a signaling device.

Figure 1:
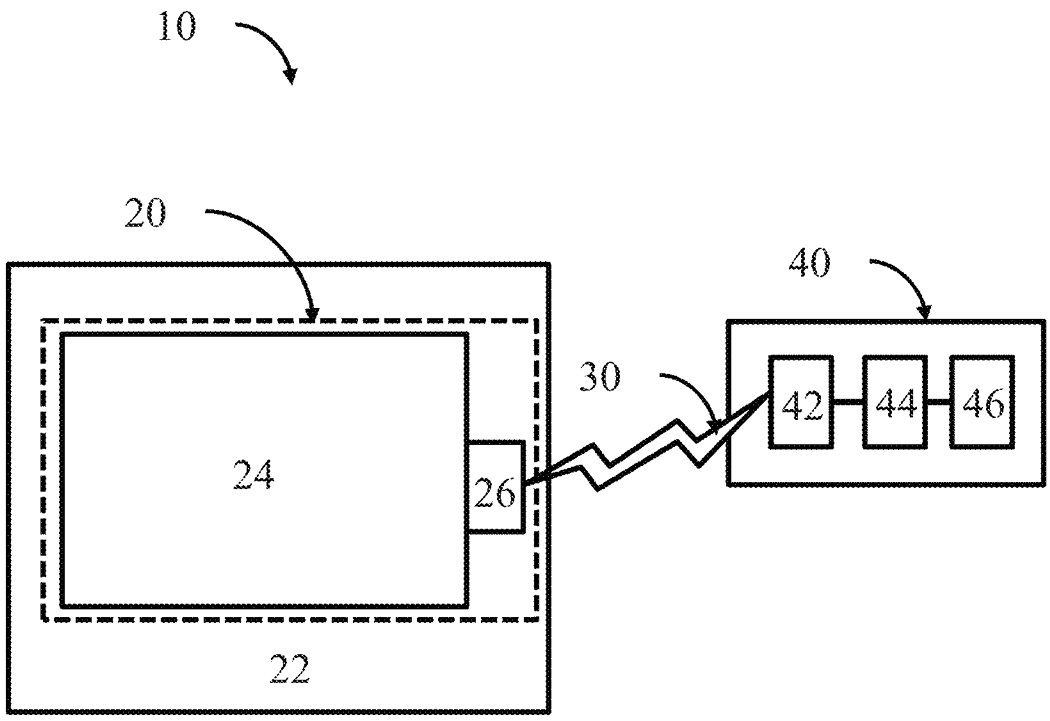
FIG. 1 is a simplified depiction of one embodiment of the present invention.

As shown in FIG. 1, the system (10) is generally comprised of a moisture detection and signaling device (the "Signaling Device") (20), which is intended as an enhancement to sanitary articles (22) that are used to absorb bodily wastes such as urine and feces, including incontinence pads and incontinence briefs, diapers, and feminine sanitary products, and a receiving and indicating device (the "Reader") (40), which could include a smartphone or tablet computer, but includes at least a microphone (42) and a processor (44), and optionally some component for outputting results (46), such as a display, an Ethernet port, a wi-fi transceiver, or other component capable of communicating the results from the processor to a person or another device.

The Signaling Device (20) is generally comprised of five elements: (1) the sensing element (the "Sensing Element"), (2) the impedance measuring circuit (the "Impedance Measuring Circuit"), (3) the oscillator circuit (the "Oscillator"), (4) the acoustic transducer (the "Transducer"), and (5) the power supply source (the "Power Supply"). The device may additionally be comprised of a timer ("Timer"), and one or more visual signaling components, such as an electroluminescent signaling diode (the "LED Signal").

The Signaling Device typically is separated into two portions: a first portion (24) that comprises the Sensing Element, and a second portion (26) that comprises the remaining elements.

Figure 2:
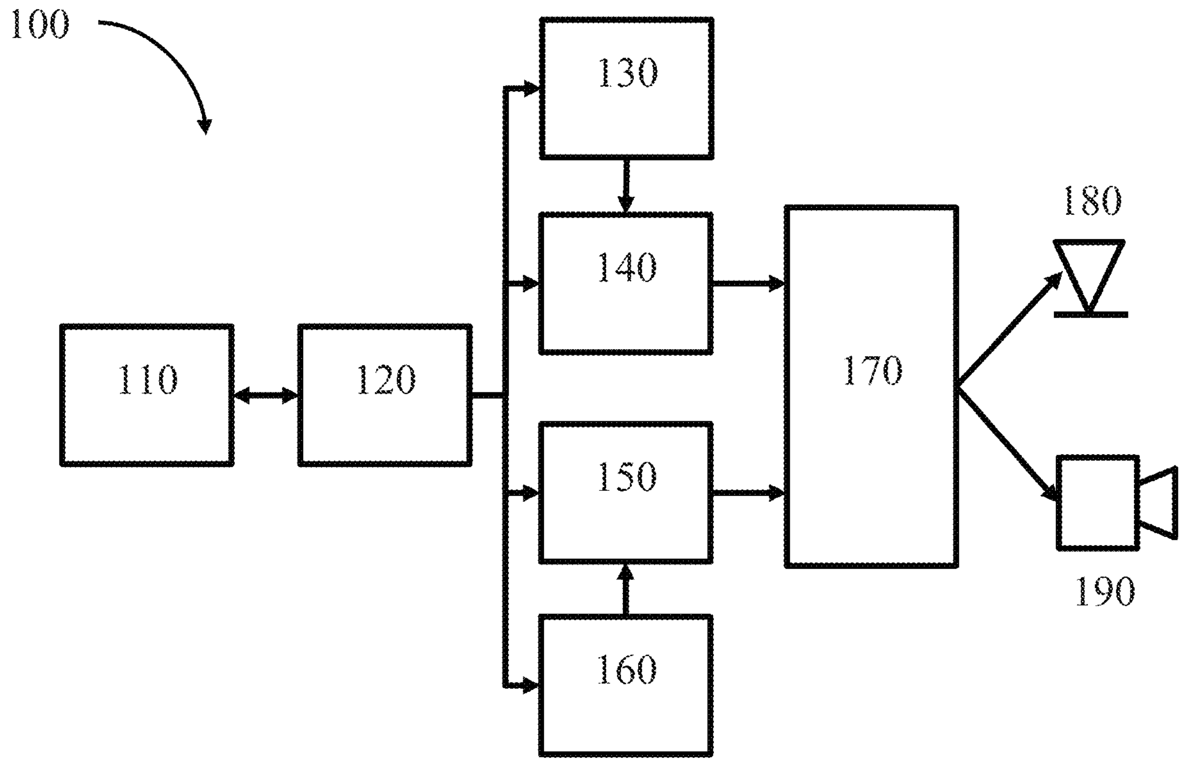
FIG. 2 is a block diagram of a Signaling Device.
Figure 3:
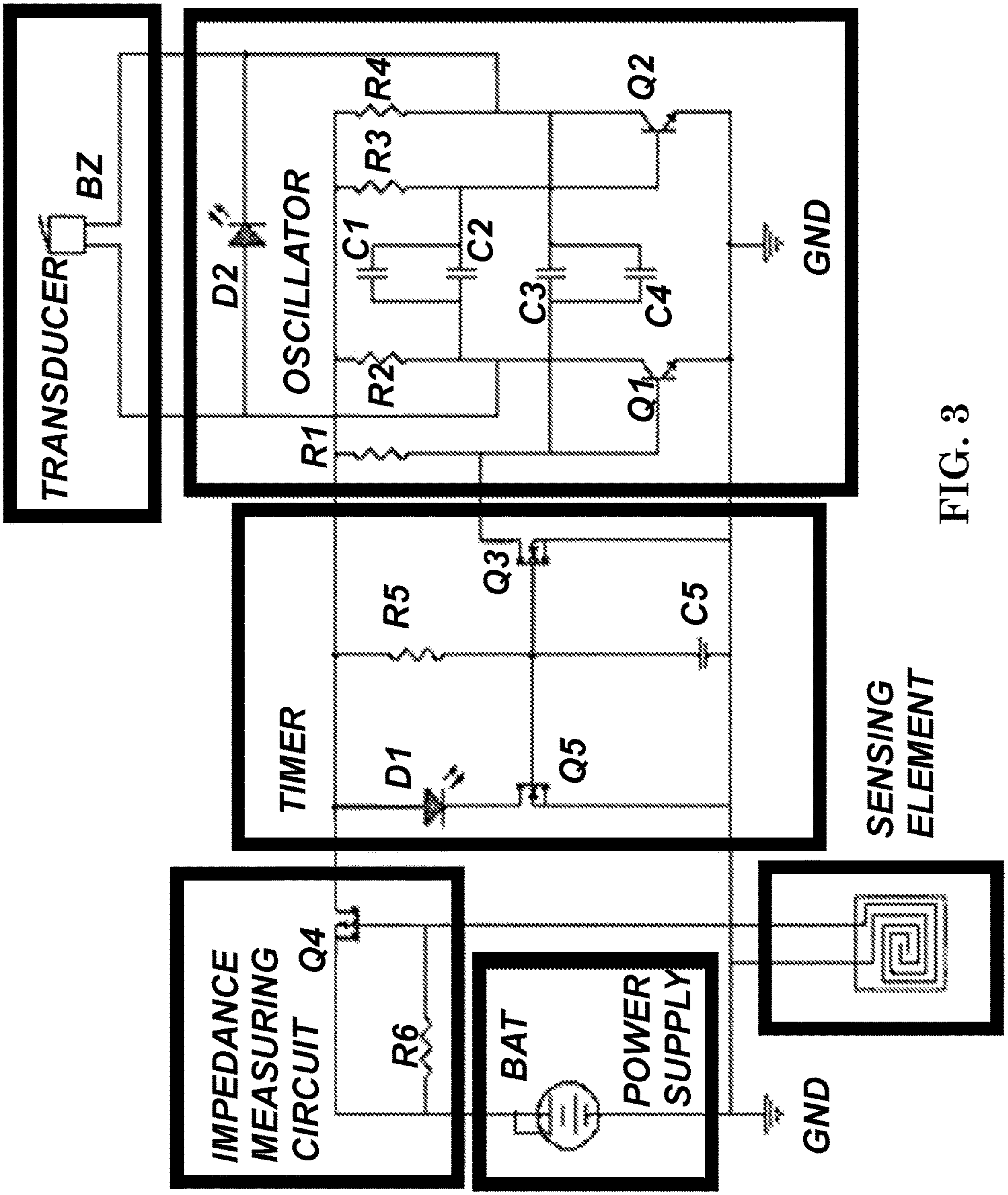
FIG. 3 is a depiction of a Signaling Device schematic.

As shown in FIGS. 2 and 3, in preferred embodiments the sensor impedance (110) is measured by the Sensing Element (20) and detected by the Impedance Measuring Circuit (120). This generates a signal which is passed to the LED drivers (140), transducer driver and Oscillator (150), and/or timers for the drivers (130, 160). The LED driver (140) and transducer driver and Oscillator (150) in turn send signals to the I/O drivers (170). The I/O drivers (170) cause the LED Signal (180) and/or Transducer (190) to operate.

The Sensing Element (20) is a pattern of electrodes that detects changes in the electrical impedance (typically, resistance) between its terminals when it comes in contact with an electrolyte-containing bodily fluid, such as urine, feces or blood.

Figure 4:
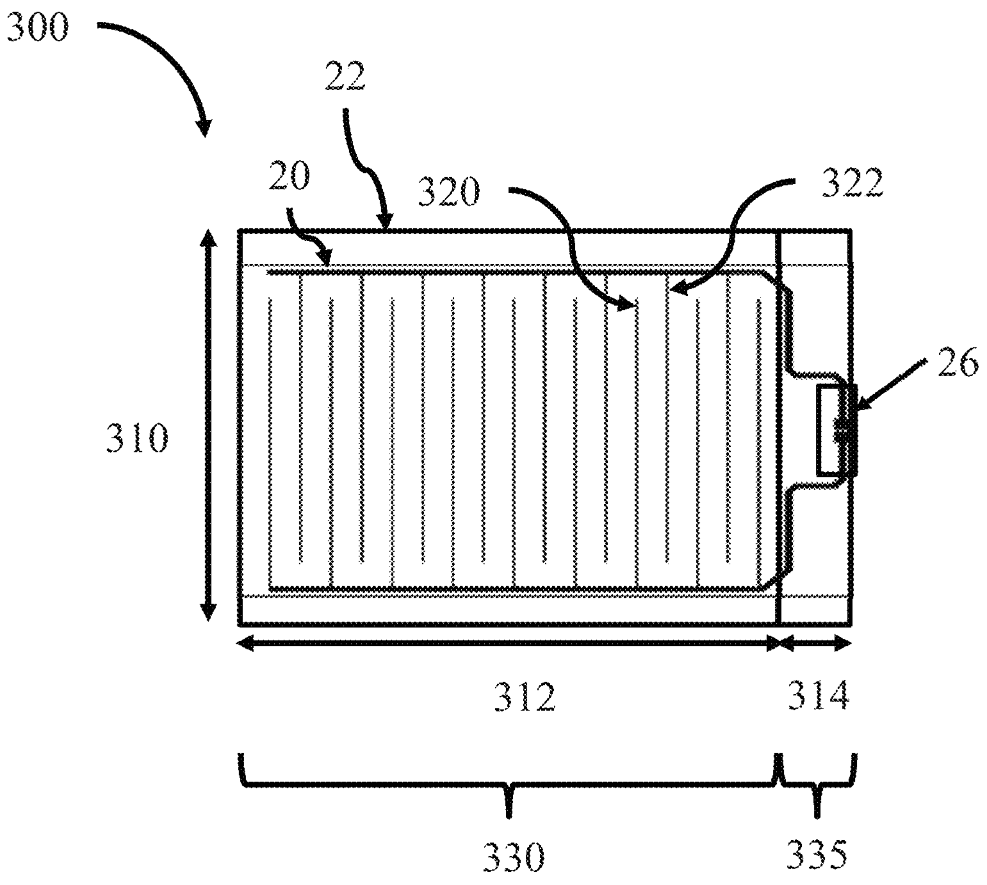
FIGS. 4 and 5 are depictions of particular components of a Signaling Device.
Figure 5:
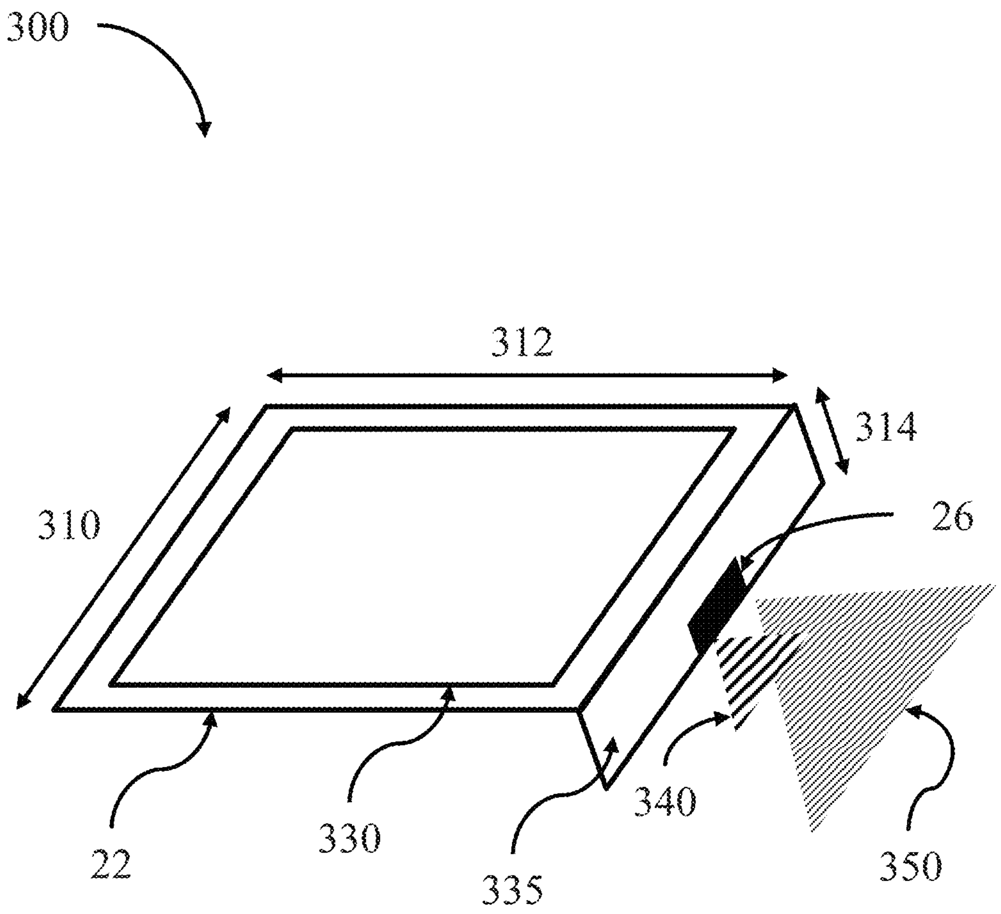

As shown in FIG. 4, this element (20) can be an interdigitated pattern of conductive electrodes applied to one of the interior facing layers of a sanitary article (22). The main portion (22) of a sanitary article has a typical defined length (310) and a width (312). For example, sanitary disposable underpads are typically about 30" long by 36" wide. In preferred embodiments, the Sensing Element (20) is typically positioned in the main portion (330) of the sanitary article. However, the remaining elements of the Signaling Device are located on an extended portion (335) of the sanitary article (22) that extends a distance (314) beyond the typical width (312). Often, this distance is between 2 and 8 inches, and preferably between 4 and 6 inches. As illustrated in FIG. 5, in preferred embodiments the main portion of the sanitary device (330) can be placed on a patient support device, such as a bed or chair, and the extended portion (335) is able to hang over the edge of a patient support device, where it is unlikely to be covered by the patient's body or limbs. This allows the other electronic components in the second portion (26) of the Signaling Device to operate more effectively, such as allowing a visual signal (340) or audio signal (350) to emit without impairment.

Figure 6:
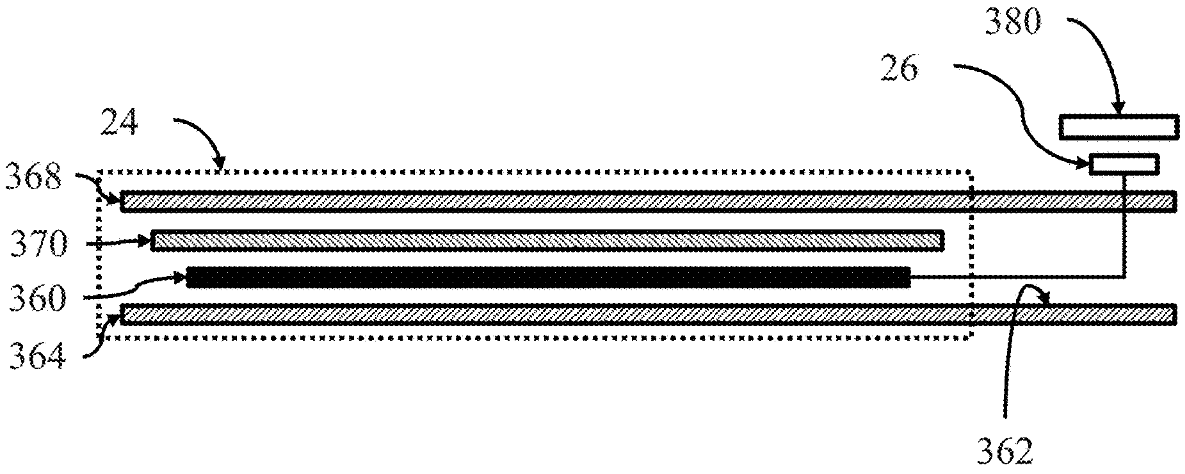
FIG. 6 is an illustration of a side view of a Signaling Device.
Figure 7:
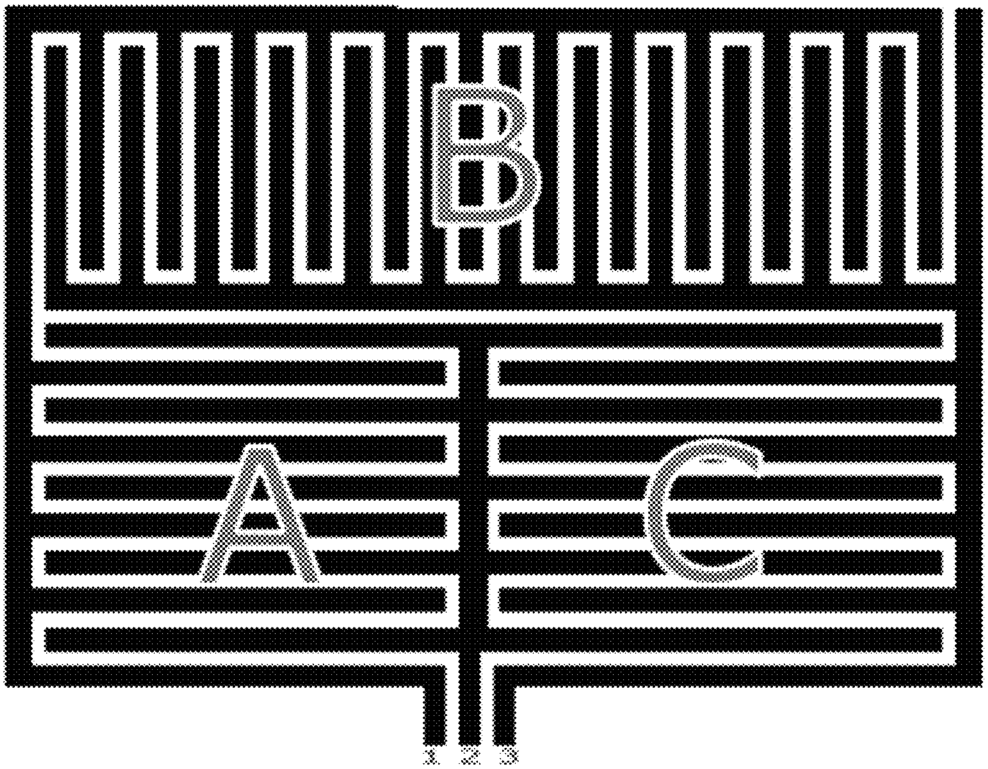
FIGS. 7-10 are illustrations of multi-zone electrode patterns.
Figure 8:
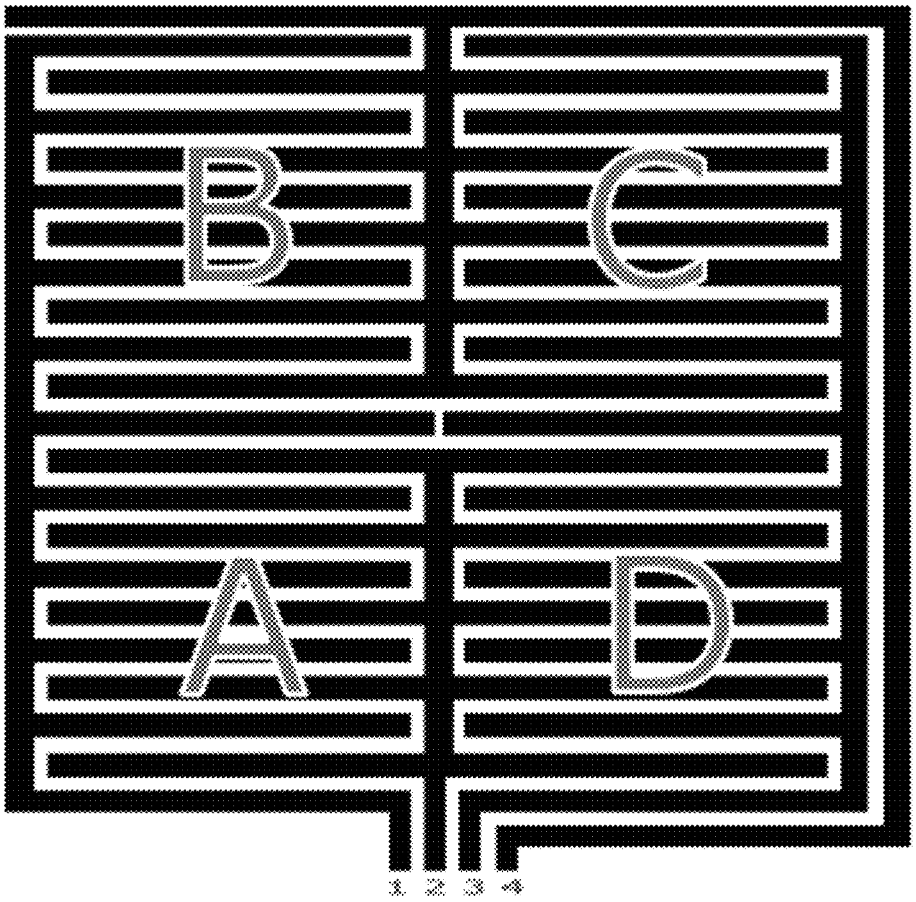
Figure 9:
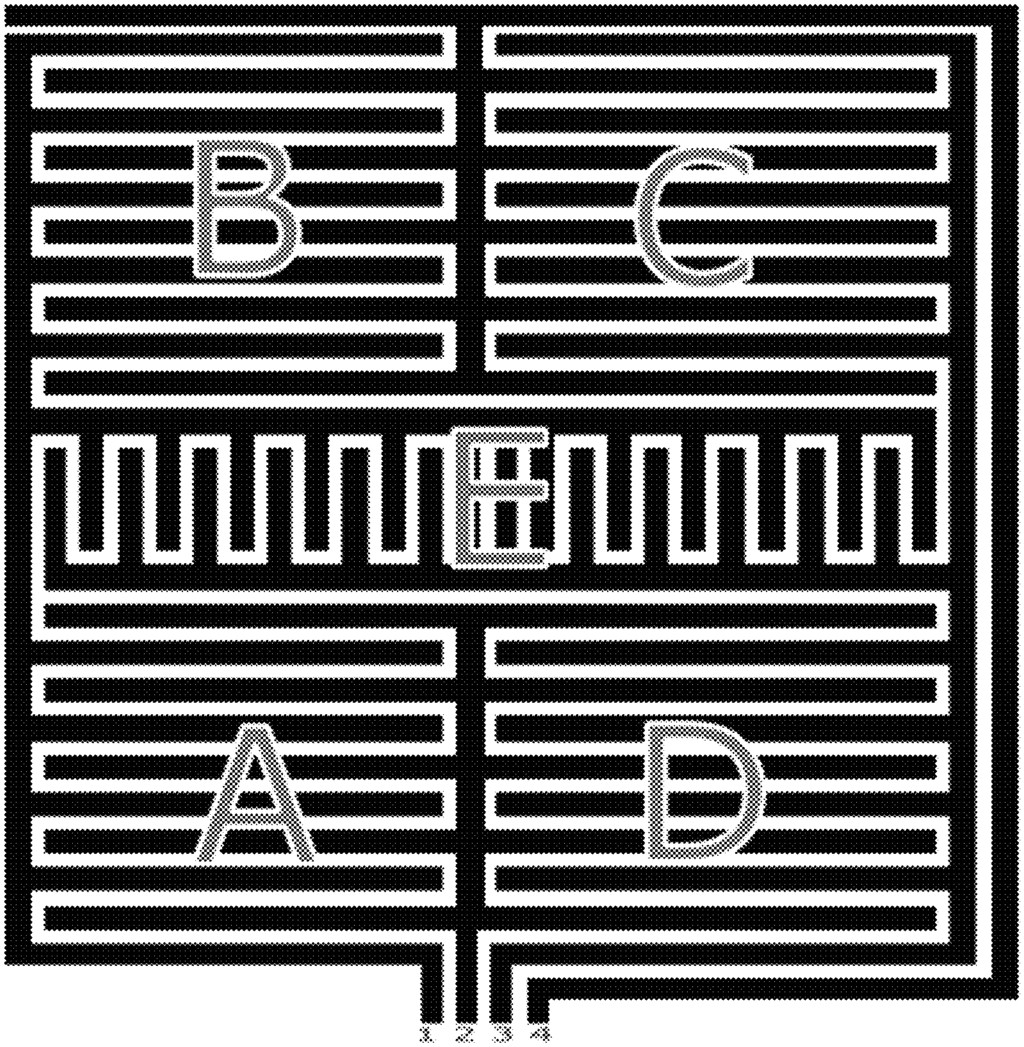

A side-view of an embodiment of the Sensing Element can be seen in FIG. 6. A conductive pattern (360) is shown on the interior facing surface (362) of a first substrate (364) that typically is not directly contacting the patient. Additional substrate(s) (368), including an absorbent material layer(s) (370), may also be included. In FIG. 6, a second portion (26) is shown, electrically connected to the conductive pattern (360). The second portion (26) is typically located at a distance from the conductive patterns (360), and may be located on the first substrate (364) or one of the additional substrate(s) (368). A protective layer (380) may also be utilized to protect the second portion (26) from moisture or biofluids. In some embodiments, the second portion (26) may be encapsulated by the protective layer (380).

The conductive patterns of the Sensing Element may be manufactured using a variety of methods. One embodiment of a method uses a selective metallization technique. A simplified description of this technique involves three steps: (i) printing a mask on the surface of a non-conductive substrate that is to be used as one layer within sanitary article; (ii) depositing a conductive metal (such as, but not limited to, aluminum and copper) on the same surface of that non-conductive substrate via vacuum deposition; and (iii) removing the deposited metal in the area where the mask was printed (e.g., washing). Another embodiment involves the printing of conductive ink on the surface of a non-conduction substrate. In certain embodiments, the vacuum-deposited metal or printed conductive ink used in forming the electrodes may optionally be doped, alloyed, or otherwise combined with specific chemical formulations that react with and thus allow for the detection of a specific analyte or analytes within the biofluid. Subsequently, such a reaction causes a measurable shift in the signal produced by the Sensing Element, which in turn can be detected, interpreted, reported and record by the system. Such analytes may include traces of and/or biomarkers indicative of pharmaceuticals, alcohol, controlled substances or disease states. Upon reacting with the specific chemistry in the doped conductive ink electrodes, the generated signal may be shifted or attenuated in frequency, amplitude or shape in such a way that the system is able to determine the presence, volume or concentration of the analyte of interest.

The spacing of the interdigitating between one "finger" (320) and a second "finger (322) determines the threshold volume of moisture required to trigger the system. Typically, this spacing will be between 2 and 8 inches, and more preferably between 4 and 6 inches.

Figure 10:
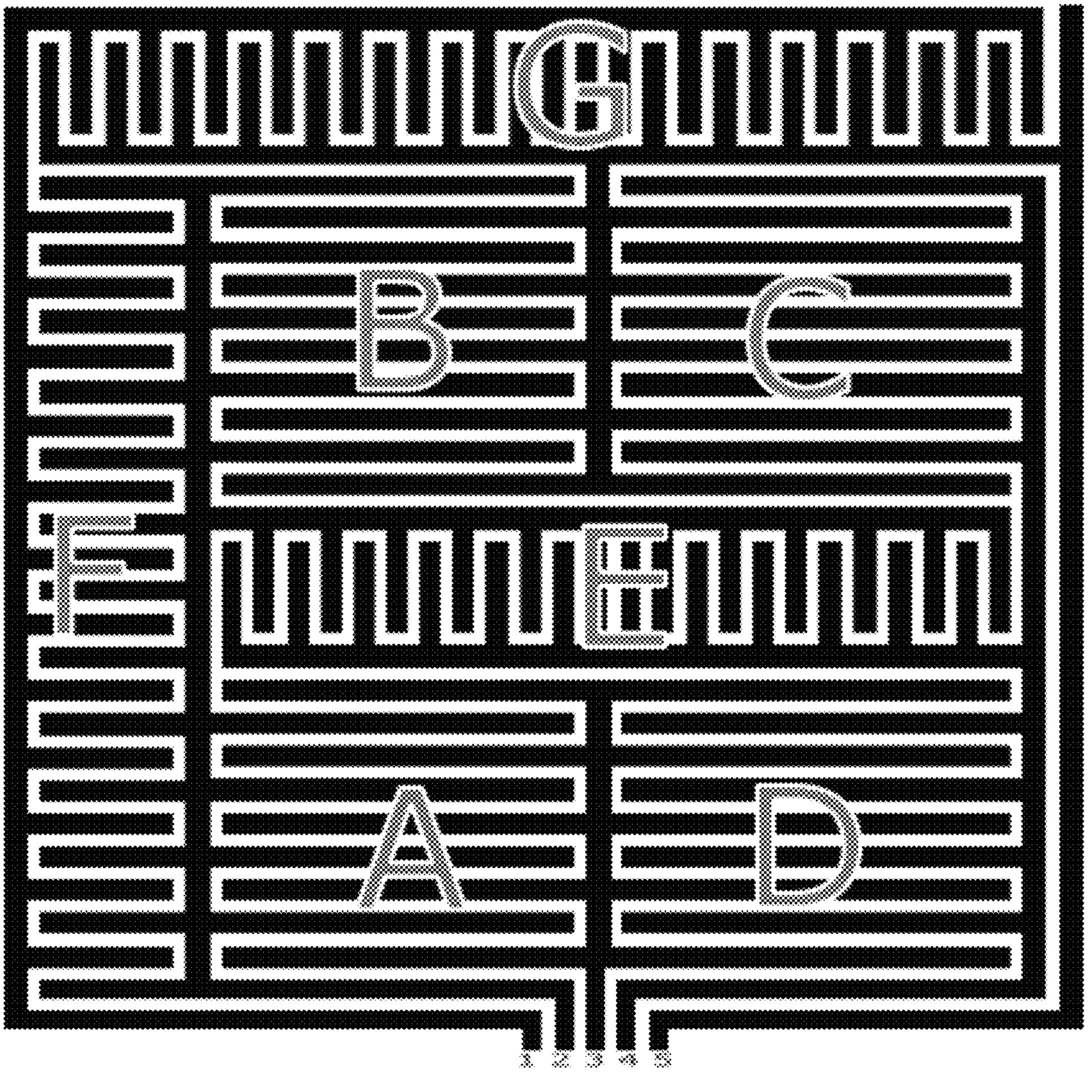

This system may also use "zones" of electrodes (see FIGS. 7-10) to provide additional detail surrounding the wetness event. For example, a wetness event detected by a single zone (e.g., "A" in FIG. 10) may indicate only a small volume of liquid is present, while if it is detected by three zones (e.g., Zone "A", "D", and "E" in FIG. 10), significantly more volume could be present.

In some embodiments, the system may be adapted to avoid picking up "small" spots of wetness. What defines "small" will be relative to the application—in some applications, "small" can be spots less than 5 or 6 inches in diameter, while in other applications, "small" spots may be defined with smaller (e.g., 4 inch, 2 inch, or 1 inch) or larger (e.g., 8 inch, 10 inch, or 12 inch) diameters. For example, what constitutes a small amount of urine in a sanitary article intended for use by an infant may be different than what constitutes a small amount of urine in that intended for use by an adult, and what is acceptable for human use may be different than what is acceptable for use in an animal pen.

Normally, these systems operate by having the fluid complete the circuit between the two electrodes. The fluid has a resistance much greater than that of the electrodes, so as distances between electrodes increases, the power requirements increase greatly, which may be undesirable for some applications. One approach to avoiding this issue is to create "bridges". This approach is illustrated in FIG. 11.

Figure 11:
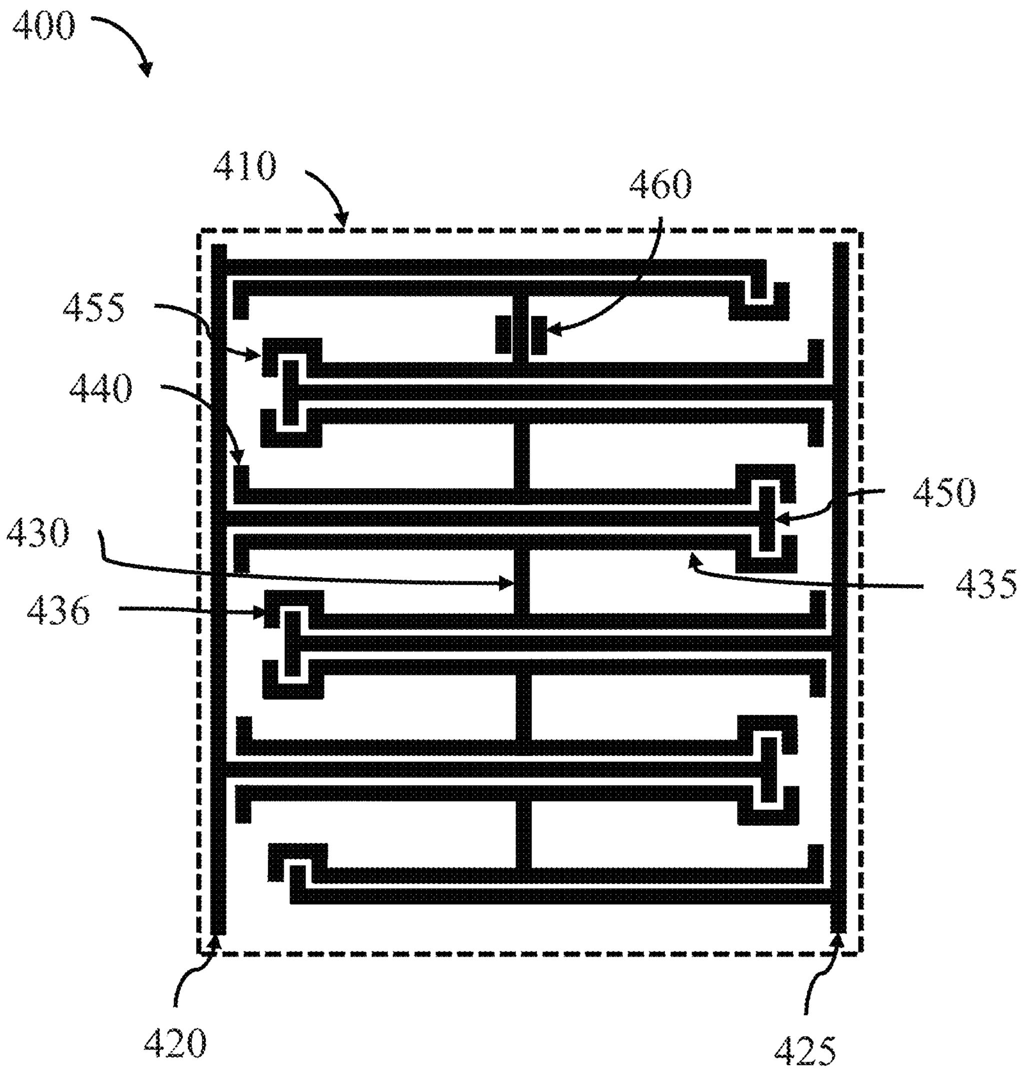
FIG. 11 is a depiction of an electrode pattern having a bridge configuration.

FIG. 11 illustrates a sensing element (400) utilizing a substrate (410) having two interdigitated conductive electrodes (420, 425).

Consider the spacing between the fingers on interdigitated conductive electrodes (420, 425), defined as a distance "D". If a spot of fluid is smaller than D, the switch described by the system would always be open, and no spot will be detected that is smaller than that distance. On the other hand, if the spot is larger than 2*D (that is, the spot covers two fingers from the same interdigitated conductive electrode), then regardless of its position on the surface, the switch is always closed, which triggers a signal that fluid is detected. Sizes that are in between D and 2*D would have a smaller or greater probability to close the switch.

In practical cases, an open switch means that the resistance (R) measured between nodes of the interdigitated conductive electrodes (420, 425) is higher than an arbitrarily large value, for example 10 Mega Ohms. A closed switch would be measuring an R smaller than that value, for example measuring 1 Mega Ohms. When the electrodes are present on, for example, a disposable underpad, without urine they show a normally expected residual resistance that has a very large value, typically above 1 Giga Ohms.

"Ohms per square" is a commonly-used measure of resistivity in surface resistors. A 5 Mega Ohms per square resistivity means that when one uses electrodes spaced at 1 inch, a resistance of 5 Mega Ohms will be measured when the urine in contact with the electrodes creates a square of 1 inch dimension. Experiments with urine present on a disposable underpad for various embodiments indicate that for those embodiments, urine creates a resistivity that has a value of about 1-5 Mega Ohms per square.

It is generally preferable to have threshold values in the range of 1-100 Kilo Ohms. A situation requiring detecting open/closed conditions with a threshold above 1 Mega Ohms creates challenges in particular for low cost detection circuits. For example, consider an embodiment having two (2) conductive nodes spaced at a 5-inch distance and a circular urine spot of 6 inch diameter that is centered exactly midway between the two nodes. A virtual rectangle is formed, having a length of 5 inches (the vertical distance between the nodes) and a width of 3.317 inches (in this example, the horizontal distance between the two points on each node where the circle crosses that node). If the resistivity of the urine is 5 Mega Ohms per square, the resistance of that spot would be 5*5/3.317 or about 7.538 Mega Ohms.

A method exists that allows that resistance to be reduced, while keeping the separation between conductive nodes. Conceptually, this method is illustrated in the simplified schematic shown in FIGS. 12A and 12B. It can be considered adding a conductive material between fingers of the interdigitated conductive electrodes, filling the majority of the gap without closing the switch between nodes. The conductive material creates a third electrical node (520), and the spacing (physical separation) (513, 518) between the fingers (512, 517) of electrodes (510, 515) and the third electrical node (520) is very small, preferably less than 1 inch, more preferably less than 0.5 inches, still more preferably less than 0.1 inches, and most preferably 0.02 inches or less. Using the arrangement described previously, where the spot (505) had a resistance of 7.538 Mega Ohms, if a third electrical node is added with spacing (513, 518) between fingers (512, 517) and third electrical node (520) of 0.02 inches, this resistance drops significantly. Using this method, the electrical resistance between node 510 and 515 is composed of 3 elements: R1, R2 and R3, as shown in FIG. 12B. The first resistor, R1, is the same resistance as described previously—7.538 Mega Ohms. The second and third elements are connected in series through third electrical node 520 and have a value R2, R3 equal to R2=R3=5*0.02/3.317=0.030 Mega Ohms. Their equivalent combined series resistance is therefore 59.824 Kilo Ohms (R=R1*(R2+R3)/(R1+R2+R3)=59.824 Kilo Ohms).

Using the example of 5 inch separation, if the urine spot is smaller than the 5 inch separation between fingers (512, 517), this urine spot would not cover at least one of the gaps between the third electrical node (520) and at least one finger, leaving the switch in open state. Similarly, a spot larger than ten inches (i.e., 2*5 inches) would be guaranteed to make contact with all three nodes, regardless of its position in the sensing area. While FIG. 12A presents only one conductive area that creates only one electrical node (520), this is merely a simplification for illustration purposes; in practice, the conductive area is typically repeated into every space available between fingers, creating multiple additional electrical nodes.

It is worth noting that the resistance measured dropped by a factor of 100 while the size of the spot that creates a positive signal remains the same. The 0.02 inch separation between nodes C and A, and between nodes C and B can be increased or decreased, depending on the technology available; as the distance is reduced, the value of the combined R resistance will be further reduced as well.

Figure 12A:
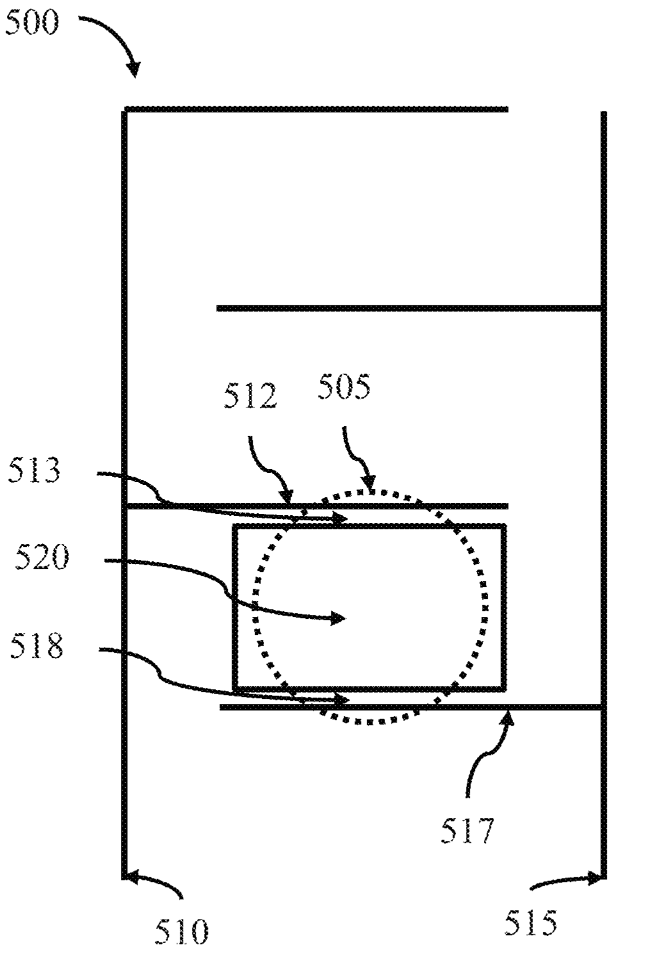
FIG. 12A is a depiction of a bridge configuration with a fluid spot.
Figure 12B:
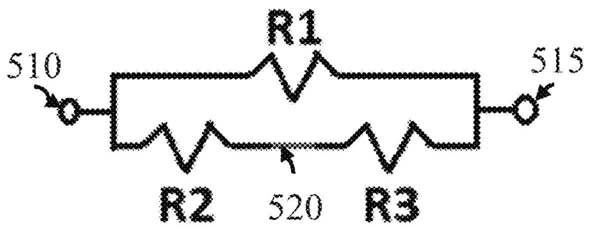
FIG. 12B is a depiction of a circuit defined by a bridge configuration.

Still considering FIGS. 12A and 12B, R2 and R3 are created by the presence of the conductors in the close vicinity of fingers 512 and 517, respectively. It is not necessary to completely fill the gap between the fingers. As seen in FIG. 11, the gap may also be filled by other structures. In FIG. 11, at least one bridge (430) is also on the substrate (410) between conductive elements (435, 436) that are positioned substantially parallel to, but not touching, successive fingers of the two conductive electrodes (420, 425). The space between a finger of an electrode and the closest conductive element (435) is significantly smaller than the gap between the two closest conductive elements (435, 436). While the bridge (430) is shown here in an "H" type pattern and runs perpendicularly between the conductive elements, this is not a requirement, and other embodiments may utilize practically any other pattern, including but not limited to "Z" type patterns, "C" type patterns, "S" type patterns, and curved patterns. In some embodiments, the bridge (430) may have additional portions (460) that are positioned at a distance from the bridge itself. In some embodiments, the conductive elements (435, 436) may have portions (440) that are at some distance from non-interdigitated portions of the conductive electrodes (420, 425). Further, in some embodiments, it may be advantageous to have an extended portion of the fingers (450) that extends towards other fingers. FIG. 11 shows a "T" shaped end to the fingers, although other configurations, including but not limited to a "Y" shape, or a box shape, may be utilized. In those instances, the conductive elements (435, 436) are typically configured to have portions (455) that partially surround the extended portion of the fingers (450). The lines of the bridges and related elements do not need to be straight lines, nor particularly parallel. One of skill in the art can create various shapes that would emphasize the detection of smaller spots in some areas of interest. In any of those cases, adding an additional node to reduce the resistance measured between fingers would fall into the description of this invention.

In operation, a large spot that covers two successive fingers will form a circuit by conducting from a first conductive electrode (420), through a small portion of fluid covering the gap between a finger and the closest conductive element (435), through the conductive element (435) to the bridge (430) and across to the opposing conductive element (436), through another small portion of fluid covering to gap between the conductive element (436) and the closest finger, and finally to the second conductive electrode (425). By having the conduction primarily occur through highly conductive materials as opposed to a fluid, the power requirements may, in some applications, be kept low.

The Impedance Measuring Circuit measures the impedance, and in preferred embodiments the resistance, of the Sensing Element and turns on the Oscillator upon some threshold condition(s), such as the expected impedance corresponding to, for example, 50 mL of urine contacting the Sensing Element.

Figure 13B:
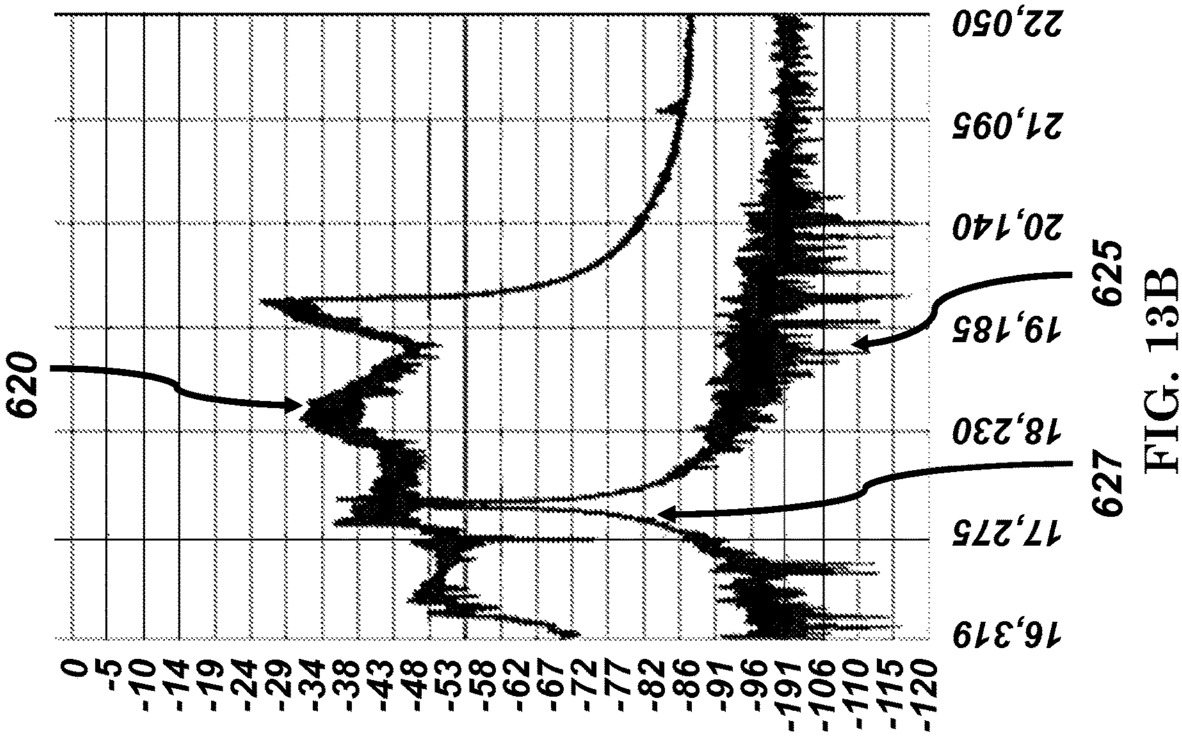
FIGS. 13A and 13B are peak and real-time signal amplitudes generated by embodiments of a Transducer across a range of frequencies and recorded by a Reader.
Figure 13A:
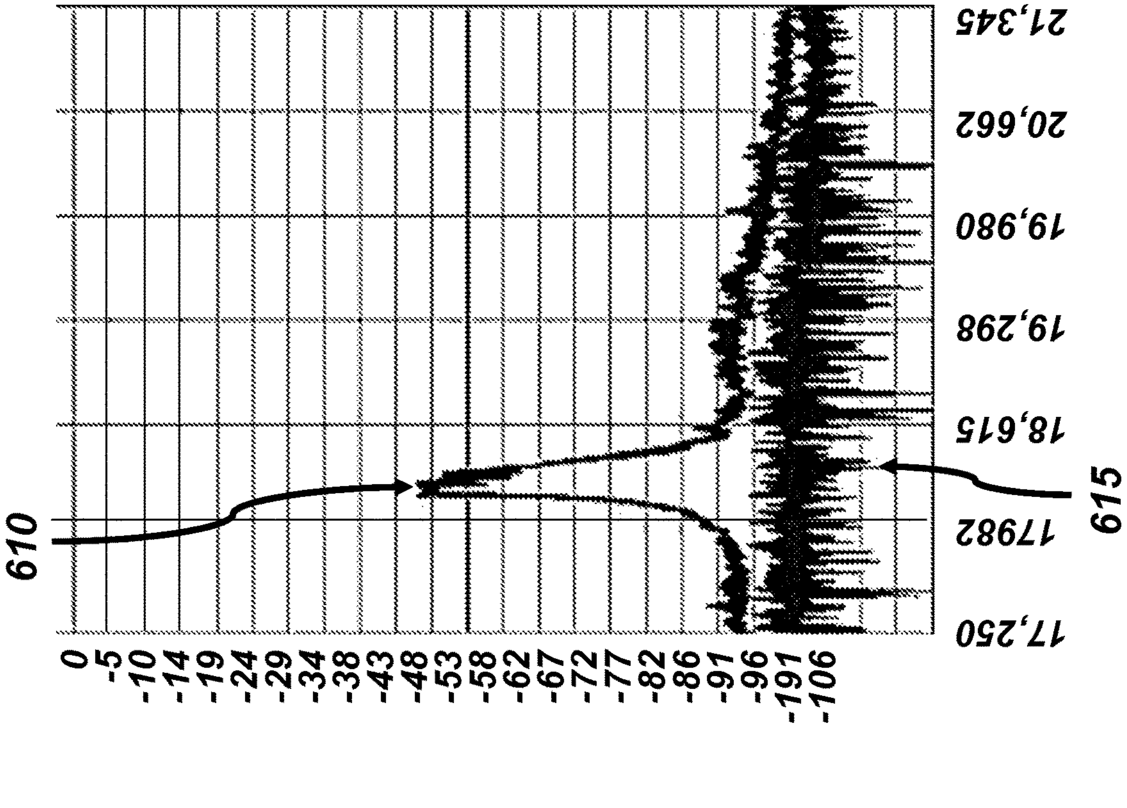

The Oscillator produces alternating currents (or voltages) at predetermined frequencies and amplitude. The Oscillator drives the Transducer, which produces an acoustic signal. The Transducer is understood to be a device that converts electrical signals into acoustic signals (vibrations of air). A preferred embodiment of the Transducer is a piezoelectric device. The amplitude of the signal produced by the Oscillator determines the intensity of the acoustic signal produced by the Transducer. The frequency can be relatively fixed (such as 19.6 kHz+/−0.1 kHz) or sweeping (such as sweeping between 17.6 kHz+/−0.2 kHz and 20.6 kHz+/−0.2 kHz). The 19.6 kHz+/−0.1 kHz refers to the accuracy of producing such frequency with common electronic devices, in this case being about 0.1 kHz higher or lower than the target frequency of 19.6 kHz. The acoustic signal produced by the Transducer is in the highest range of human audible signals (and is likely inaudible to most adult humans) or the lower ultrasonic frequency range. The peak signal amplitudes can be seen in FIGS. 13A and 13B, where they appear as the upper set of data (610, 620). As shown in FIG. 13A, one embodiment of the Transducer can generate a fixed frequency, centered on a frequency of approximately 18.3 kHz. FIG. 13B shows another embodiment of the Transducer, where the Transducer is set to generate a frequency sweep from about 16.3 to about 20 kHz. The real-time data—the lower set of data (615, 625)—appears as a spike (627) at about 17.6 kHz only because the screen shot was recorded while the frequency sweep was in progress. FIG. 13A does not show such a spike because the screen shot was captured after the Transducer was deactivated.

Common methods of building the Oscillator and Transducer include an electronic multi-vibrator circuit built with bipolar junction transistors, resistor, capacitors, and a piezoelectric transducer. The Oscillator produces electric currents (voltages) of given frequencies that drive the Transducer to produce an acoustic signal at the same frequency as the Oscillator. The multi-vibrator can also generate a range of frequencies to produce a "frequency sweeping" acoustic signal. The benefit of such frequency sweeping is to align the frequency produced by the Oscillator to the frequency at which the Transducer produces the highest peak of acoustic intensity in conjunction with its surrounding materials (e.g., blankets, sheets or mattress surface), which can interact with the Transducer and alter frequency resonance and amplitude. This is important because, in practical implementation, it is impossible to know in advance the exact surrounding materials with which the Transducer will interact and the exact nature of the interaction. Frequency sweeping thus substantially improves the likelihood of adequate signal-to-noise ratio (SNR). For example, a thermal snag free blanket made of a 55% Cotton/45% Polyester blend with a tight-woven box pattern may cause a shift in signal frequency and amplitude when lightly pressed against the Transducer on the side of a bed. In some instances, if the Transducer were to generate a signal at only one frequency, e.g., 18 kHz, this could result in an inadequate signal-to-noise ratio ("SNR"). However, the signal may be affected much less at a different frequency, e.g., 19 kHz. Thus, by sweeping a range of frequencies, the probability of achieving adequate SNR at some frequency within the range is substantially improved. Frequency sweeping also solves for the inherent variance when assembling acoustic transducer systems. Typical performance variance is +/−10% for the generated frequency due to variances in the Transducer itself and how it is mounted onto a circuit board, and it requires expensive componentry or manufacturing techniques to reduce variance. For instance, if the system is designed to work at a single frequency, e.g., 18 kHz, in practicality, the signal may range from ~16-20 kHz. Frequency sweeping thus eliminates normal variance as a hindrance to a cost- and performance-effective system.

Other methods include a bipolar junction transistor, resistors and self-resonating acoustic transducers. Other methods could use two inverter logic gates in a multi-vibrator configuration to drive the Transducer at its self-resonating frequency. Other methods of combining oscillating circuits and acoustic transducers are known in the industry.

In the preferred implementation, the frequency is swept between 16 kHz-20 kHz, which the very upper range of the human audible spectrum. This frequency range is often non-audible to adult humans, and can be picked up by common devices such as smartphones or tablets. For example, a Samsung Galaxy Note 5 normally samples the audio sound with 44.1 kHz and can thus detect audio signals up to 22 kHz, which is well within the preferred implementation's range. In addition, frequencies above 25 kHz can be irritating to household pets. The preferred implementation range stays below those frequencies. Finally, hearing aid devices amplify acoustic signals at frequencies up to 12 kHz. The preferred implementation range stays above that frequency and thus avoids interference with such hearing aids.

If such concerns are not taken into consideration, however, this system will function across a very broad range of frequencies, dependent on the ability to detect the acoustic signal. For example, if the Reader can sample an audio sound at 48 kHz, a signal of 24 kHz can be detected. If the Reader samples at 96 kHz, a signal of 48 kHz can be detected.

In a preferred implementation, the LED Signal is used to additionally indicate a wetness condition. Such signal could be activated simultaneously or subsequent to the acoustic signal of the Transducer. The LED Signal could be stopped after a time period or kept active until the Power Supply's energy is depleted (without energy, all the signaling processes would stop). This is useful to indicate which Signaling Device was activated if there are multiple sanitary articles being monitored in close proximity, such as in a single room or in adjoining rooms. Also, if a caregiver is away from his/her device that receives notification from the Reader (e.g., the caregiver is attending to a patient while the caregiver's PC, which may have received an electronic notification of a wetness condition, remains outside the room), the LED Signal will alert him nonetheless. Finally, the LED Signal is a non-intrusive way for family members visiting a hospital room to detect a wetness condition for a loved one, even if they do not receive the electronic notification from the system.

In a preferred implementation, the Oscillator is stopped after a given time period, such as one minute to minimize the probability of overlapping signals with other nearby Signaling Devices. This embodiment includes the Timer, a simple circuit that employs a resistor, a capacitor and an N-channel MOSFET device to stop the Oscillator. The resistor charges the capacitor, and when the voltage on the capacitor reaches the threshold of the MOSFET device, that device acts as a switch that turns off the Oscillator. The Timer also includes a separate MOSFET to turn on the LED Signal.

In more complex configurations, the acoustic signal generated by the Transducer can be modulated by a controlling device and such modulation can be used to determine specific conditions. For example, a serial number could be stored in a small memory, and that serial number could be used to modulate the intensity, frequency or duration of pulses of the sound signals. The Reader could detect such modulation and recover the serial number. A variety of modulation schemes exist in the state of the art and the ones mentioned above are examples. Instead of a serial number one could send other types of information using the same sound carrier. Without limiting the possible applications, the Impedance Measuring Circuit could determine resistance value of the Sensing Element, which could be indicative of the volume of bodily fluid exuded by the patent, and communicate that value through a modulated acoustic signal.

Figure 14:
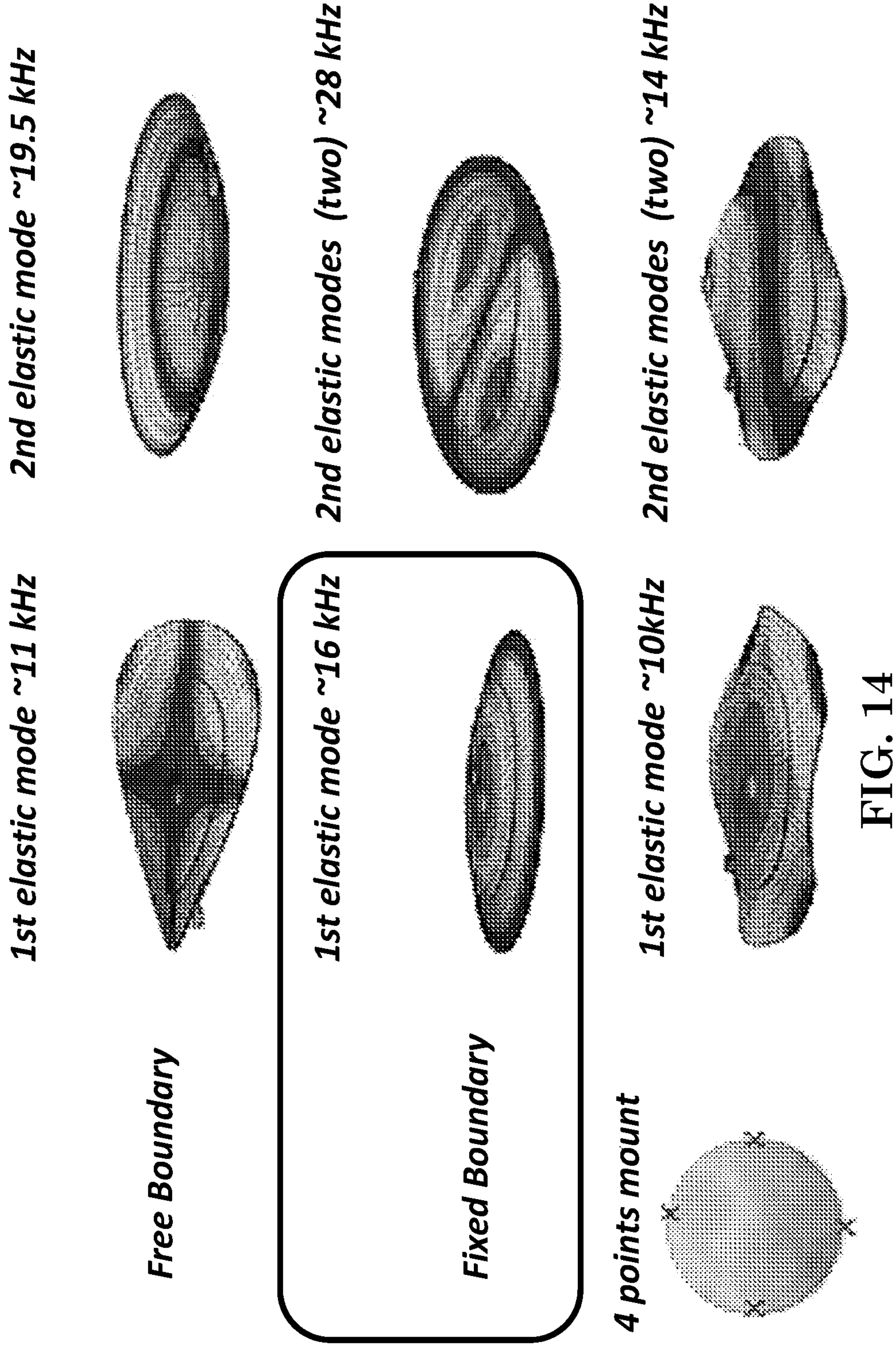
FIG. 14 is an illustration of modeling results of different methods for affixing a piezoelectric acoustic device.

As shown in FIG. 14, how the piezoelectric acoustic device is affixed to a substrate, such as a printed circuit board (PCB), impacts the performance. In preferred embodiments, the piezoelectric acoustic device is affixed along substantially the entire boundary or perimeter of the device to the substrate, while the center is left unfixed. In addition, a hole through the substrate (or other open volume of space in the substrate), interior to the boundary or perimeter, allows for maximizing the signal strength of the piezoelectric device. Thus, a preferred embodiment uses a substrate with a circular hole through the substrate, the circular hole having a diameter slightly smaller than the diameter of the piezoelectric acoustic device. The piezoelectric acoustic device is then centered over the hole to cover it completely, and the outer edges of the device are affixed to the substrate along substantially the entire perimeter of the device. The piezoelectric acoustic device may also be affixed to a different substrate such as polyethylene terephthalate (PET) or directly affixed directly to the sanitary article using an electro-conductive adhesive.

The Power Supply can be a battery or an energy-generating device. An energy-generating device could include passive RFID technology, a piezoelectric device that transforms mechanical movement into electrical energy, a photovoltaic cell, or an electro-galvanic device in which urine or another bodily fluid acts as the electrolyte. The power consumption of the Impedance Measuring Circuit is very low—in one preferred embodiment, the Impedance Measuring Circuit consumes less than 1 micro-ampere. This is important because it enables effective system performance and a long shelf-life (e.g., over one year) for battery-powered Signaling Devices using inexpensive Power Supply components.

The power supply for the Reader is generally without limitation, including but not limited to battery powered devices such as tablets or smartphones or specifically programmed devices that are plugged into an AC power source.

The application on the Reader displays may also include a smart timer which gives the time elapsed since the last wetness is detected, e.g., “Last event: 2 minutes ago.”

The Reader may operate in variety of ways, including as a single-purpose use “kiosk” mode on an Android-based tablet. In those instances, the application starts automatically when the tablet is turned ON or restarted.

From a general standpoint, Readers use a processor (44) to complete a Fast Fourier Transform (FFT) that converts a signal from a sequence of time detected by a microphone (42) and turn it from raw data into a frequency/amplitude matrix. That matrix is then manipulated to make a determination regarding whether a nearby device has indicated a wetness event has occurred.

Figure 15:
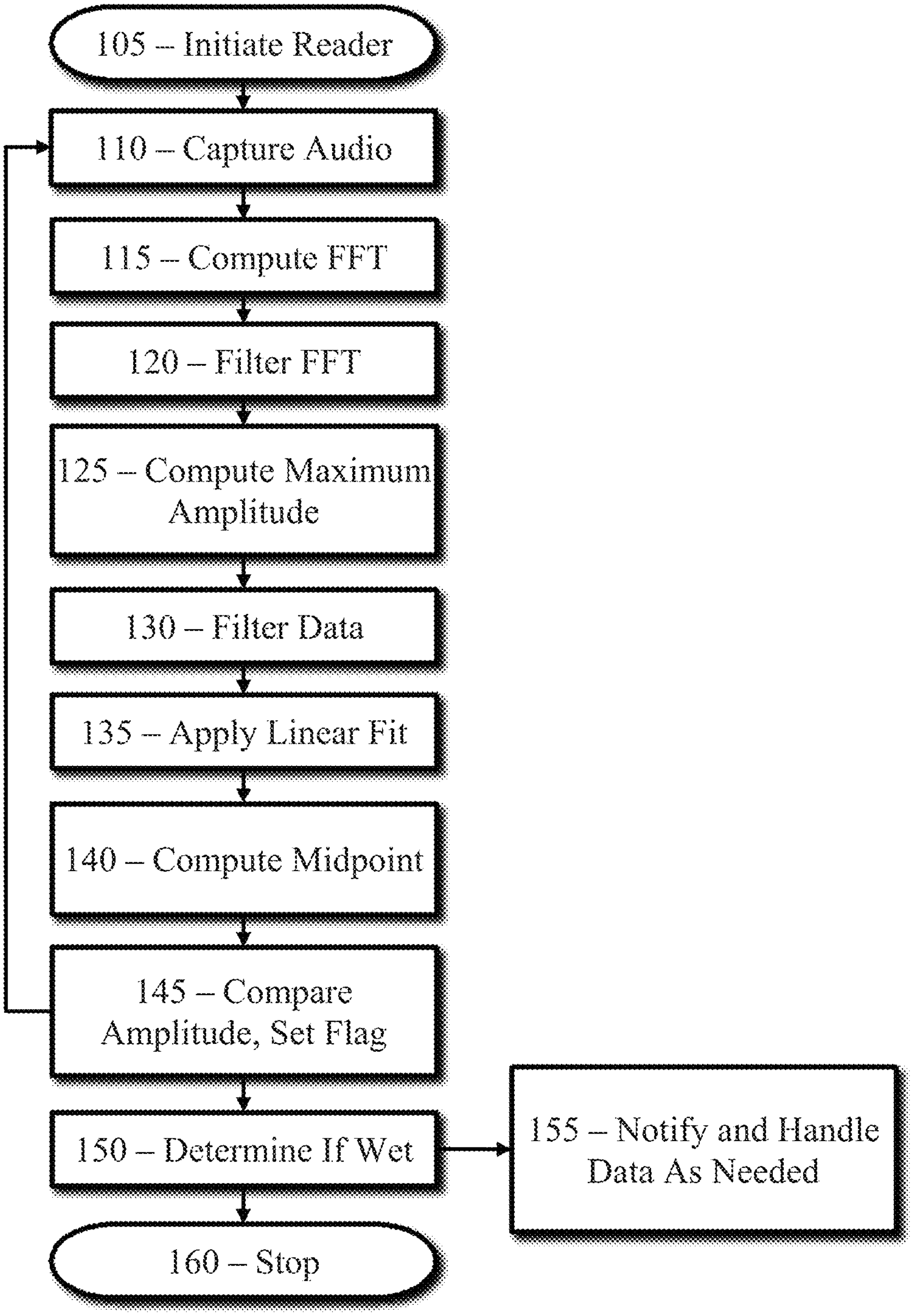
FIG. 15 is a flow diagram illustrating one embodiment of a process used by a Reader.

To minimize the effects of ambient acoustic noise and thus maximize system accuracy, the following are the operational steps of a preferred embodiment of the Reader, which is depicted in FIG. 15.

After Initiation of the Reader (105), an audio sequence is first captured (110) in a format with a sample rate of at least double the upper value of the frequency range (below), for example 44.1, 48, 88.2, or 96 kHz and an appropriate buffer size of, for example, 4096 data points.

Second, a forward FFT is applied (115) to the above data with an appropriate bin size of, for example, 2048. The result is filtered (120) to have amplitude data for a desired frequency range between, for example, 16 kHz and 20 kHz.

Third, the maximum amplitude for the above filtered data list is computed (125) and the corresponding frequency is noted as [Max(f,a)].

Fourth, the filtered data list obtained in step 120 is again filtered (130) to remove the maximum data point (obtained in step 125) and a certain number of additional data points, such as 4 data points to the left and right of the maximum data point. In this example, a total of 9 data points will therefore be removed from the filtered data obtained in step 2. This data will be denoted as [NoiseList].

Fifth, a best linear fit algorithm is applied (135) on the [NoiseList] obtained in step 130 whereby y represent the amplitude data points and x represent the frequency, and n is the number of data points. This list will be denoted by [bestfilnoistList]

$$y = b_0 + b_1 x$$

$$b_1 = \left(\Sigma xy - \frac{(\Sigma x \Sigma y)}{n}\right) \Big/ \left(\Sigma x^2 - \frac{(\Sigma x)^2}{n}\right)$$

$$b_0 = (\Sigma y - (b_1 \Sigma x)) / n$$

Sixth, compute the mid-point entry (140) [Mnoise] from the [bestfitnoistList] obtained in step 135.

Seventh, compare the amplitude of entry [Mnoise] obtained in Step 140 to a threshold (145) and set a flag. For example, if the amplitude of entry [Mnoise] obtained in Step 140 does not exceed a certain desired threshold, such as 15%, of the amplitude of entry obtained in step 125 [Max (f,a)], set peak found flag=true.

Eighth, determine if a wetness event has occurred (150). For example, Steps 1 thru 7 are executed in a repetitive fashion, and typically, a screen or indicator on the Reader is used to show that monitoring is occurring during this time. If peak found flag (such as computed in step 145) is true for a certain number of consecutive iterations, such as 5, 10, or even more consecutive iterations, the Reader implies that the a wetness event has occurred.

Various notifications and data handling routines are then utilized (155). Typically, at this time a wetness indicator is shown on the Reader. Further, the Reader may utilize SMS, email, or other form of notification, which can be enabled by entering a phone number, email address, or other contact address, on the application by navigating to a settings menu. The configured phone or email addressee would then receive, for example, an SMS or email whenever a wetness condition is detected by the Reader.

Separately, and in addition to the above, data from the Reader for each wetness event that is detected and for periodic "I am alive" status can be uploaded to a separate computer and/or database, preferably in a cloud-based storage location.

Once the Reader detects the acoustic signal, it can then relay a separate signal through a wired or wireless means (including but not limited to Wi-Fi, Bluetooth or a cellular connection) to a central computer and/or database, which can then send an electronic notification, including a text message or email alert, to a caregiver, and can also record moisture events for periodic reporting In instances where multiple Readers are used in close proximity, e.g., in adjoining rooms in an acute care or long-term care facility, the central computer can use an algorithm to attribute the wetness event to the appropriate Reader. For example, the acoustic signal triggered by a patient wetness event in one room may be detected (using the steps of the Reader as described above) by the Reader not only in that room but also by Readers in adjoining rooms. When the central computer and/or database receives indications of wetness events from multiple Readers at a particular care site within some pre-determined time threshold (e.g., 2 seconds), the computer will determine that the Readers are all responding to a single event. Then, the computer will analyze the signal intensity (amplitude) reported by each Reader to determine in which room the wetness event occurred, and it will instruct the Reader in that room only to display that an event has occurred and to send a notification via SMS or email. This is a cost-effective means, as compared to incorporating unique identifier capabilities into each Signaling Device, to pinpoint wetness events. In this example, the algorithm can be further enhanced through the use of calibration methods. One such method is for the central computer to periodically (i) instruct each Reader to generate a distinct acoustic signal and then (ii) monitor all the other Readers for the detection of that signal. By doing so with all Readers, the central computer establishes an "acoustic proximity map" across all Readers. Subsequently, when multiple Readers simultaneously detect a Transducer-generated acoustic signal, the central computer uses such a proximity map to improve its accuracy in determining the source of that signal.

The data gathered by the separate computer and/or database, as described above, can also be accessible by and displayed visually for system administrators and care managers on a secure website and via periodic reporting.

Those in the art will understand that a number of variations may be made in the disclosed embodiments, all without departing from the scope of the invention, which is defined solely by the appended claims

What is claimed is:

1. A sensing element, comprising:

a substrate;

a first conductive pattern on the substrate;

a second conductive pattern on the substrate interdigitated with the first conductive pattern; and a plurality of third conductive patterns on the substrate, each third conductive pattern electrically isolated from the first and second conductive patterns and configured such that at least a first portion of the third conductive pattern is closer to the first conductive pattern than to the second conductive pattern, and at least a second portion of the third conductive pattern is closer to the second conductive pattern than to the first conductive pattern.

2. The sensing element according to claim 1, wherein the sensing element further comprises at least one molecule configured to react with a specific analyte or analytes within a biofluid.

3. The sensing element according to claim 1, wherein the conductive patterns have been applied via selective metallization.

4. The sensing element according to claim 1, wherein the conductive patterns utilize conductive ink.

5. A biofluid detection system comprising:

a signaling device comprising:

a sensing element;

an impedance measuring circuit;

an oscillator circuit;

an acoustic transducer; and a power supply source; and a reader device comprising:

a microphone; and a processor, wherein the processor is configured to complete a Fast Fourier Transform, and filter the results of the transform to have amplitude data for a predetermined frequency range, wherein the predetermined frequency range has a lower limit of no less than 12 kHz, and wherein the reader device is further configured to determine a maximum amplitude for the filtered results, calculate a best linear fit of a dataset consisting of the filtered results from the transform minus a data point corresponding to the maximum amplitude and at least one additional data point, determine a mid-point entry based on the best linear fit, and determine if the mid-point entry does not exceed a predetermined threshold of the maximum amplitude of the filtered results.

6. The biofluid detection system according to claim 5, wherein the predetermined frequency range is between 16 and 20 kHz.

7. The biofluid detection system according to claim 5, wherein the signaling device further comprises a visual indicator.

8. The biofluid detection system according to claim 5, wherein the signaling device further comprises a timer.

9. The biofluid detection system according to claim 5, wherein the predetermined threshold is 15%.

10. The biofluid detection system according to claim 5, wherein the reader is further configured to compare a plurality of sequential samples of filtered results.

11. The biofluid detection system according to claim 5, wherein the acoustic transducer is configured to produce a signal of a type selected from the group consisting of a fixed target frequency and a frequency sweep.

12. A method of determining a wetness event has occurred, comprising:

a. measuring an impedance of a plurality of electrodes;

b. activating an oscillator if an impedance greater than or equal to a first predetermined threshold is detected;

c. producing an acoustic signal corresponding to signals from the oscillator;

d. receiving the acoustic signal;

e. completing a Fast Fourier Transform using the received acoustic signal;

f. filtering results of the transform to have amplitude data for a predetermined frequency range;

g. determining a maximum amplitude for the filtered results;

h. calculating a best linear fit of a dataset consisting of the filtered results from the transform minus a data point corresponding to the maximum amplitude and at least one additional data point;

i. determining a mid-point entry based on the best linear fit; and j. determining if the mid-point entry does not exceed a second predetermined threshold of the maximum amplitude of the filtered results.

13. The method according to claim 12, further comprising repeating steps d-j and signaling a wetness event has occurred if the mid-point entry does not exceed a predetermined threshold of the maximum amplitude of the filtered results a predetermined number of times.

14. The method according to claim 13, wherein the first predetermined threshold is a value corresponding to the impedance of 50 mL of urine, the predetermined frequency range is 16 to 20 kHz, the second predetermined threshold is 15%, and the predetermined number of times is 5.

* * * * *